US009040715B2

(12) United States Patent
Calderone et al.

(10) Patent No.: US 9,040,715 B2
(45) Date of Patent: May 26, 2015

(54) 1,2-BENZISOTHIAZOLINONE AND ISOINDOLINONE DERIVATIVES

(75) Inventors: Richard A. Calderone, Chevy Chase, MD (US); William C. Groutas, Wichita, KS (US); Brent E. Korba, Laurel, MD (US)

(73) Assignee: Georgetown University, Washington, DC (US)

( * ) Notice: Subject to any disclaimer, the term of this patent is extended or adjusted under 35 U.S.C. 154(b) by 918 days.

(21) Appl. No.: 13/120,602

(22) PCT Filed: Sep. 23, 2009

(86) PCT No.: PCT/US2009/058067
§ 371 (c)(1),
(2), (4) Date: Jun. 23, 2011

(87) PCT Pub. No.: WO2010/039545
PCT Pub. Date: Apr. 8, 2010

(65) Prior Publication Data
US 2011/0251193 A1 Oct. 13, 2011

Related U.S. Application Data

(60) Provisional application No. 61/099,412, filed on Sep. 23, 2008, provisional application No. 61/179,444, filed on May 19, 2009, provisional application No. 61/220,936, filed on Jun. 26, 2009, provisional application No. 61/220,958, filed on Jun. 26, 2009.

(51) Int. Cl.
C07D 275/04 (2006.01)
C07D 417/06 (2006.01)
C07D 417/12 (2006.01)
C07D 417/04 (2006.01)

(52) U.S. Cl.
CPC ............ *C07D 275/04* (2013.01); *C07D 417/06* (2013.01); *C07D 417/04* (2013.01); *C07D 417/12* (2013.01)

(58) Field of Classification Search
USPC ........................................................ 548/209
See application file for complete search history.

(56) References Cited

U.S. PATENT DOCUMENTS

| 3,761,489 A | 9/1973 | Grivas |
| 4,041,042 A | 8/1977 | Fabian et al. |
| 4,113,728 A * | 9/1978 | Baggaley ...................... 546/146 |
| 6,667,316 B1 | 12/2003 | Man et al. |
| 2003/0109559 A1 | 6/2003 | Gailunas |
| 2005/0069541 A1* | 3/2005 | Karlik et al. ............... 424/143.1 |
| 2007/0219218 A1 | 9/2007 | Yu et al. |

FOREIGN PATENT DOCUMENTS

| GB | 1271 054 A | 4/1972 |
| WO | 01/46183 A1 | 6/2001 |
| WO | WO 01/42216 | 6/2001 |
| WO | 2006/020879 A1 | 2/2006 |
| WO | 2006/091858 A1 | 8/2006 |
| WO | WO 2006/116713 | 11/2006 |
| WO | WO 2006/117306 | 11/2006 |
| WO | WO 2008/077597 | 7/2008 |
| WO | WO 2008/084240 | 7/2008 |
| WO | WO 2008/099165 | 8/2008 |
| WO | WO 2008/151183 | 12/2008 |
| WO | WO 2009/010478 | 1/2009 |

OTHER PUBLICATIONS

Dolle et al., Angewandte Chemie, International Edition (2005), 44(36), pp. 5830-5833.*
Chemical Abstracts Registry No. 902871-26-5, indexed in the Registry file on STN CAS Online Aug. 21, 2006.*
Chemical Abstracts Registry No. 902840-95-3, indexed in the Registry file on STN CAS Online Aug. 20, 2006.*
Slawik, CA 117:171291, 1992.*
Slawik, CA 115:114496, 1991.*
Mahmoud, A.M. et al., Synthesis and biological activities of some new 2-(N-heterocyclic carboxamidomethyl thio) benzoxazoles, benzthiazoles and benzimidazoles. Part VIII. Eur. J. Med. Chem.—Chimica Therapeutica, Jul.-Aug. 1981, 16(4), pp. 383-384.
John W. Scott et al.; "3,5-Dialkyl-4-(phthalimidomethyl)isoxazoles, pyrazoles, and isothiazoles. Novel antiandrogens"; Journal of Medicinal Chemistry, vol. 16, No. 5; May 1, 1973;pp. 512-516, XP55023780; p. 514; compound 37.
Rufer C. et al: "Neue Acylierte 2-(4-Aminophenyl)-Propionsaeuren Als Potentiele Antiphlogistica"; European Journal of Medicinal Chemistry, Editions Scientifique Elsevier, Paris, FR; vol. 13, No. 2; Mar. 1, 1978; pp. 193-198, XP001068547.
Thierry Aubert et al.; "Nouvelle voie de 1,2synthese d'isoindolones et d'isoquinoleines par condensation d'iminophosphoranes avec 1 'ortho-phtalaldehyde: reactions, mecanismes et etude structurals"; Canadian Journal of Chemistry;vol. 68, No. 6; Jun. 1, 1990; pp. 842-851, XP55023778.
Roland E. Dolle et al.; "Solid/Solution-Phase Annulation Reagents: Single-Step Synthesis of Cyclic Amine Derivatives"; Angewandte Chemie International Edition; vol. 44. No. 36; Sep. 12, 2005; pp. 5830-5833, XP55023776.
Thomas J Schwan et al.; "Synthesis of Antifungal 2-Substituted Phthalimidines" J of Pharmaceutical Science;vol. 67, No. 6; Jun. 1, 1978; pp. 863-864, XP001465016.
Breytenbach, J.C. et al.;. "Synthesis and Antimicrobial Activity of Some Isoindolin-1-ones Derivatives" Bioorganic and Medicinal Chemistry Letters; vol. 10, 2000; pp. 1629-1631. XP002673634.
Mor M et al: "Biologocal studies on 1,2-benzisothiazole derivatives. V. Antimicrobial properties of N-akanoic, N-arylalkanoic and N-aryloxyalkanoic derivatives of 1,2-benzisothiazolin-3-one: QSAR study and genotoxicity evaluation"; Farmaco, Societa Chimica Italiana, Pavia, IT; vol. 51, No. 7; Jan. 1, 1996; pp. 493-501, XP009158306.

* cited by examiner

*Primary Examiner* — Laura L. Stockton
(74) *Attorney, Agent, or Firm* — Kilpatrick Townsend & Stockton, LLP

(57) ABSTRACT

Novel classes of 1,2-benzisothiazolinone and isoindolinone compounds and compositions are disclosed. These compounds and compositions are useful in treating, preventing, and/or ameliorating viral, yeast, and fungal infections such as, for example, Hepatitis C Virus, Flavivirus infections, *Aspergillus fumigatus*, and candidiasis.

16 Claims, 4 Drawing Sheets

1,2-BENZISOTHIAZOLINONE AND ISOINDOLINONE DERIVATIVES

BACKGROUND

Viral, yeast, and fungal infections are major causes of morbidity and mortality. For example, chronic infection with hepatitis C virus (HCV) is a major health problem that affects more than 170 million people worldwide and is a causative agent of liver cirrhosis, hepatocellular carcinoma, and liver failure. Flaviviruses such as West Nile virus (WNV), Japanese Encephalitis virus, and Dengue virus (e.g., the four known serotypes of Dengue virus (DEN-1-4)) are significant human pathogens that cause millions of infections each year. Aspergillosis and Candidiasis are fungal and yeast infections that can be life threatening for those with weakened immune systems. Currently, there are no approved vaccines or antiviral therapeutics available for either DEN- or WNV-infected humans. While there are treatments for HCV, candidiasis, and aspergillosis, these treatments are plagued by limited efficacy, serious side effects, high expense, and often result in drug resistance.

SUMMARY

Novel 1,2-benzisothiazolinone and isoindolinone compounds and compositions useful in treating, preventing, and/or ameliorating viral infections (e.g., Hepatitis C Virus and Flavivirus infections) and fungal or yeast infections (e.g., candidiasis and aspergillosis) are disclosed along with methods of making and using them. A first class of compounds includes 1,2-benzisothiazolinone and isoindolinone compounds of the following formula:

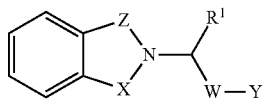

and includes pharmaceutically acceptable salts and prodrugs thereof. In this class of compounds, $R^1$ is hydrogen or methyl; W is —C(O)NR$^2$—, —C(O)NR$^3$—NR$^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; X is CH$_2$ or S; Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl; and Z is C=O or SO$_2$.

A second class of compounds includes isoindolinone compounds of the following formula:

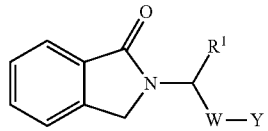

and includes pharmaceutically acceptable salts and prodrugs thereof. In this class of compounds, $R^1$ is hydrogen or methyl; W is —C(O)NR$^2$—, —C(O)NR$^3$—NR$^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A third class of compounds includes 1,2-benzisothiazolinone compounds of the following formula:

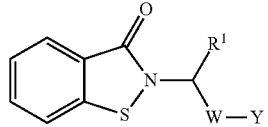

and includes pharmaceutically acceptable salts and prodrugs thereof. In this class of compounds, $R^1$ is hydrogen or methyl; W is —C(O)NR$^2$—, —C(O)NR$^3$—NR$^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A fourth class of compounds includes 1,2-benzisothiazolinone compounds of the following formula:

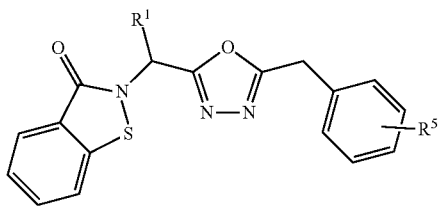

and pharmaceutically acceptable salts or prodrugs thereof. In this class of molecules, $R^1$ is hydrogen or methyl; and $R^5$ is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A fifth class of compounds includes 1,2-benzisothiazolinone compounds of the following formula:

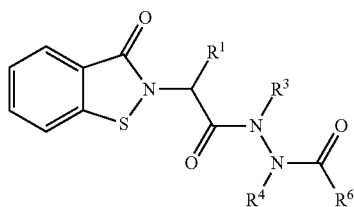

and pharmaceutically acceptable salts or prodrugs thereof. In this class of molecules, $R^1$ is hydrogen or methyl; $R^3$ and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and $R^6$ is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A sixth class of compounds includes 1,2-benzisothiazolinone compounds of the following formula:

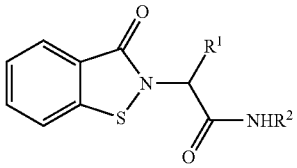

and pharmaceutically acceptable salts or prodrugs thereof. In this class of compounds, $R^1$ is hydrogen or methyl; and $R^2$ is hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A seventh class of compounds includes 1,2-benzisothiazolinone compounds of the following formula:

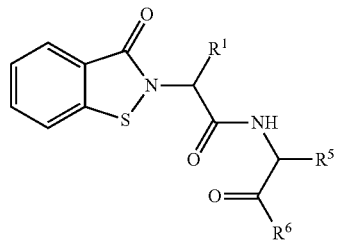

and pharmaceutically acceptable salts or prodrugs thereof. In this class of compounds, $R^1$ is hydrogen or methyl; and $R^5$ and $R^6$ are each independently selected from hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalky Also provided herein are novel compositions including the 1,2-benzisothiazolinone and isoindolinone compounds described herein and pharmaceutically acceptable carriers.

A first method for the treatment of viral infections, such as Hepatitis C and Flavivirus infections (e.g., West Nile Virus, Dengue Virus, and Japanese Encephalitis Virus), in a subject includes administering to the subject a therapeutically effective amount of the compounds and/or compositions described herein. A method for the prevention of viral infections is also provided, which includes administering to the subject a therapeutically effective amount of the compounds and/or compositions described herein. The methods of treating or preventing viral infections can further include administering a second compound or composition, wherein the second compound or composition includes an antiviral compound (e.g., a nucleoside polymerase inhibitor, a non-nucleoside polymerase inhibitor, or a protease inhibitor).

Methods of treating and preventing yeast or fungal infections, such as candidiasis-, aspergillosis-, and fluconazole-resistant infections, in a subject are also provided. The methods include administering to the subject a therapeutically effective amount of the compounds and/or compositions described herein. In some examples, the subject is immunocompromised. The methods of treating or preventing yeast or fungal infections can further include administering to the subject a second compound or composition, wherein the second compound or composition includes an antifungal, an antiviral, or mixtures thereof (e.g., a triazole, a thiazole, an imidazole, a polyene, an enchinocandin, an allylamine, a nucleoside polymerase inhibitor, a non-nucleoside polymerase inhibitor, a protease inhibitor, a nucleoside or nucleotide reverse transcriptase inhibitor, a non-nucleoside reverse transcriptase inhibitor, an entry inhibitor, an assembly inhibitor, and mixtures thereof).

DETAILED DESCRIPTION

Figure 1:
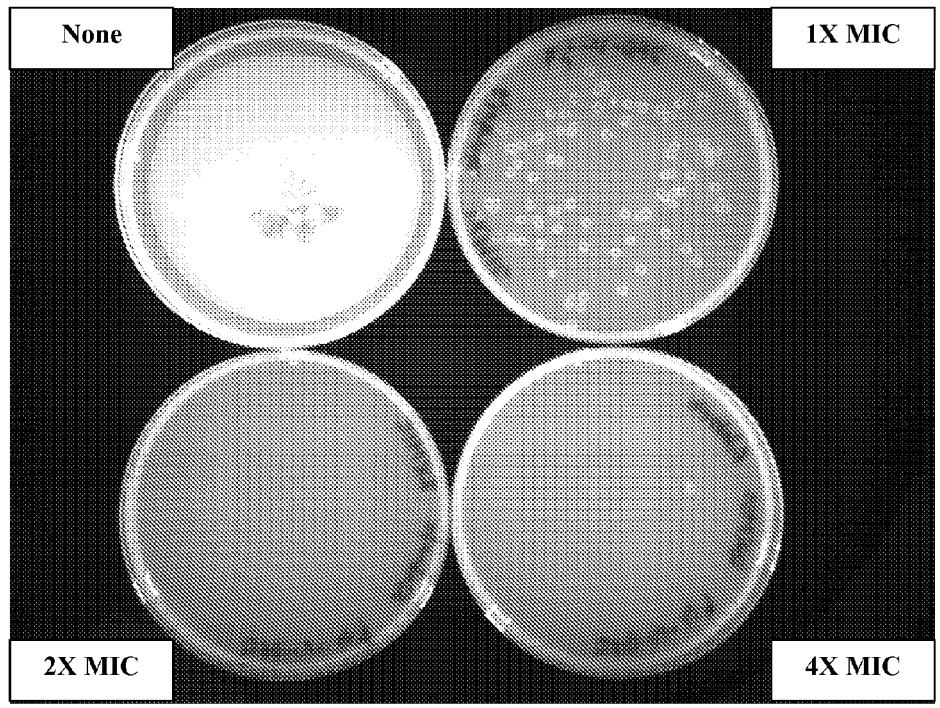
FIG. 1 is a picture of Yeast Extract/Peptone/Dextrose (YPD) plates used to determine activity by the plating method.

Described herein are novel 1,2-benzisothiazolinone and isoindolinone compounds and compositions useful in treating, preventing, and/or ameliorating viral infections (e.g., Hepatitis C and Flavivirus infections) and yeast or fungal infections (e.g., candidiasis and aspergillosis), along with methods of making and using them.

A first class of 1,2-benzisothiazolinone and isoindolinone compounds as described herein are represented by Compound I:

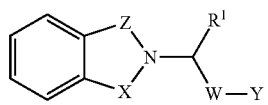

I or pharmaceutically acceptable salts or prodrugs thereof.

In Compound I, $R^1$ is hydrogen or methyl.

Also in Compound I, W is —C(O)NR$^2$—, —C(O)NR$^3$—NR$^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In some examples, W is —C(O)NH—, —C(O)NCH$_3$—, or —C(O)NH—NHC(O)—. In some examples, W is

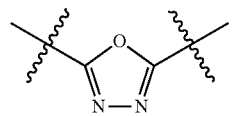

In some examples, W is —C(O)NR$^2$ and $R^2$ is hydrogen or methyl.

Additionally in Compound I, X is CH$_2$ or S.

Also in Compound I, Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, Y is substituted or unsubstituted benzyl, substituted or unsubstituted aryl, methyl, or amino.

The Y group of Compound I can have, for example, one of the following Structures A1-A4:

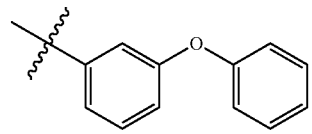

A1

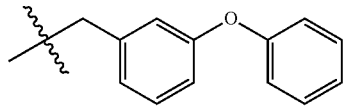

A2

A3

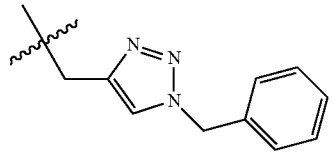

A4

Further in Compound I, Z is C=O or SO$_2$.

In some examples of Compound I, W—Y is —C(O)N(R$^2$)Y—. The —N(R$^2$)Y— group of Compound I can have, for example, one of the following Structures B1-B16:

B1
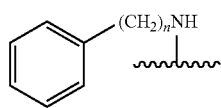
wherein n is 0, 1, or 2.
B2
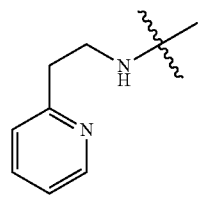
B3
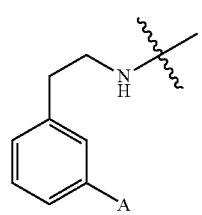
wherein A is F or OCH₃.
B4
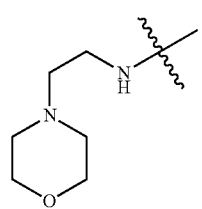
B5
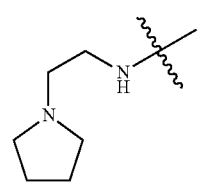
B6
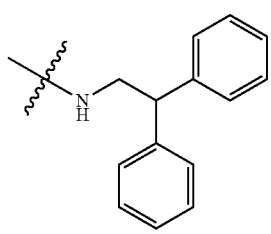
B7
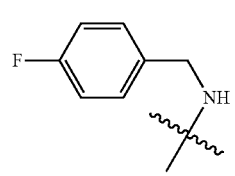
B8
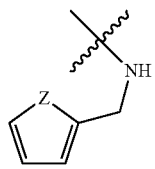
wherein Z is O or NH.
B9
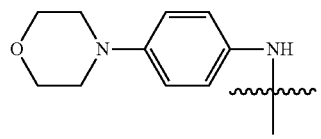
B10
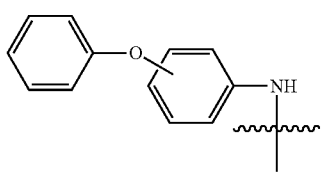
As shown in Structure B10, the phenoxy group can be in the ortho, meta, or para position.
B11
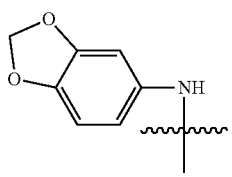
B12
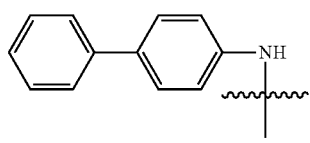
B13
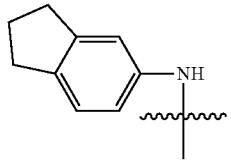
B14
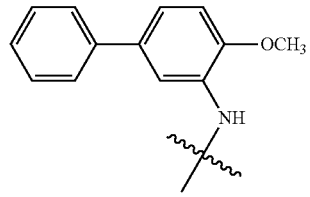
B15
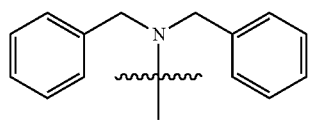

-continued

B16
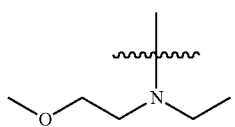

In Compound I, when W is —C(O)NR²—, the R² and Y groups can be combined to form substituted or unsubstituted aryl, substituted or unsubstituted heteroaryl, substituted or unsubstituted cycloalkyl, or substituted or unsubstituted heterocycloalkyl groups. For example, R² can be a propyl amine group and Y can be an ethyl group that combine to form a piperidine group. Further examples of the —N(R²)Y— group of Compound I wherein W—Y is —C(O)N(R²)Y—, and R² and Y combine are shown in the following Structures B17-B19:

B17
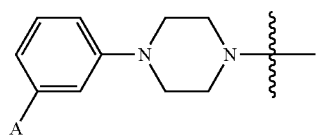

wherein A is H, —OCH₃, or CF₃.

B18
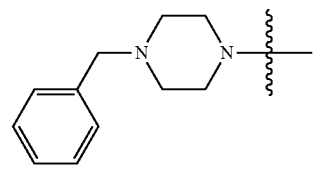

B19
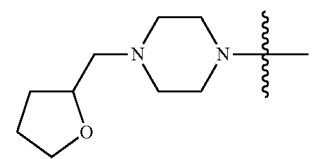

In one example of Compound I, when Z is C=O and R¹ is methyl, W—Y is not

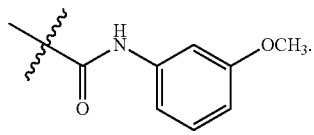 [SMILES: *C(=O)Nc1cccc(OC)c1]

In an additional example of Compound I, when Z is C=O, X is S, and R¹ is H, W—Y is not

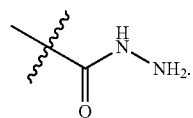

In a further example of Compound I, when Z is C=O, X is S, and R¹ is methyl, W—Y is not

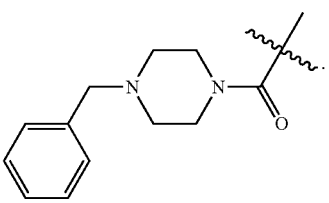 [SMILES: *C(=O)N1CCN(Cc2ccccc2)CC1]

Additional examples of Compound I are as follows:

I-1
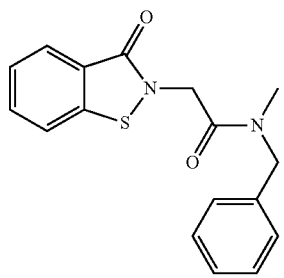

I-2
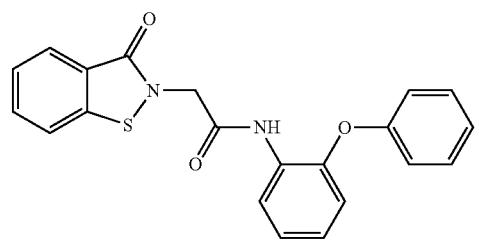

I-3
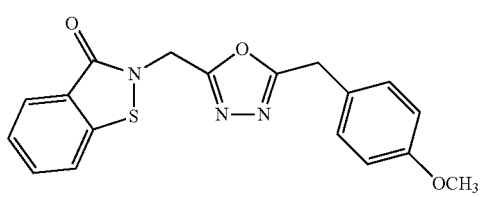

I-4
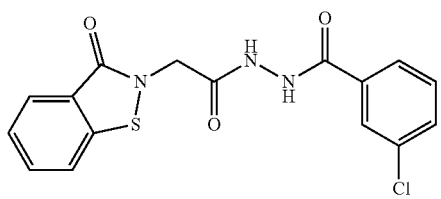

I-5

I-6
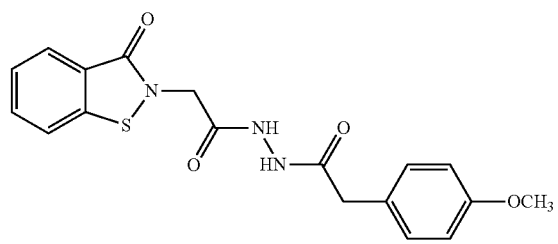
I-7
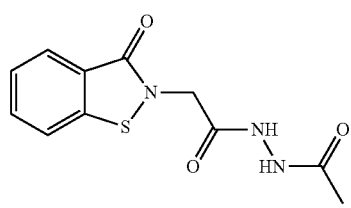
I-8
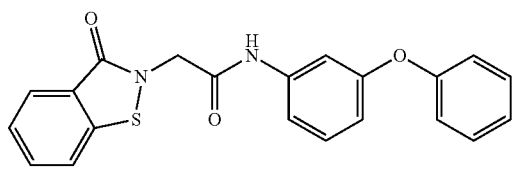
I-9
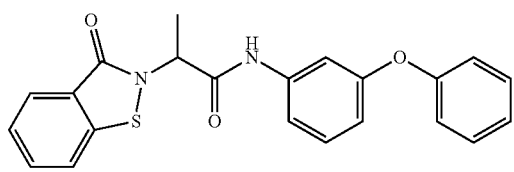
I-10
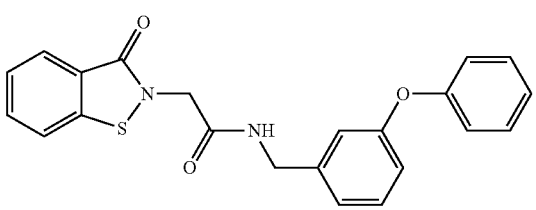
I-11
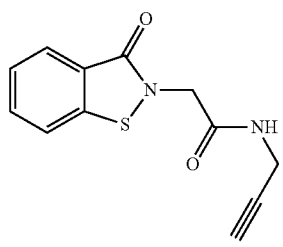
I-12
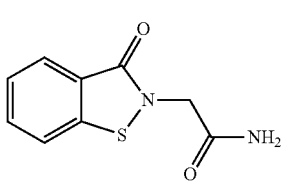
I-13
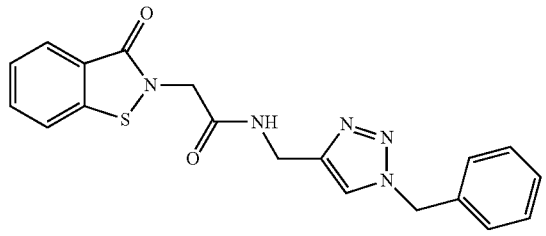
I-14
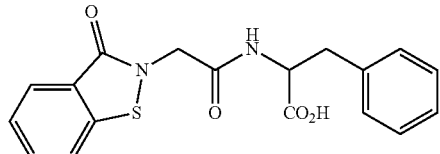
I-15
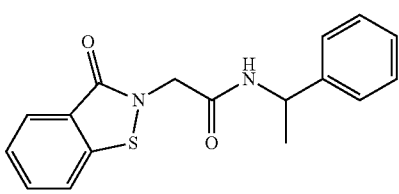
I-16
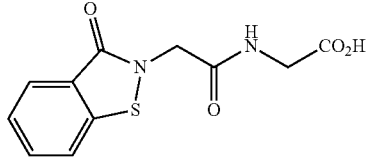
I-17
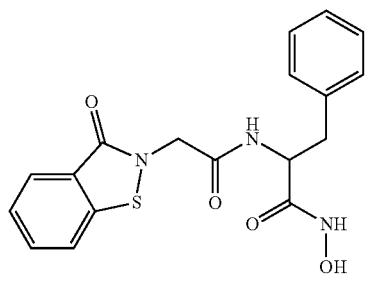
I-18
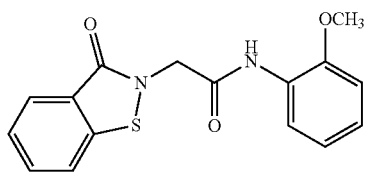
I-19
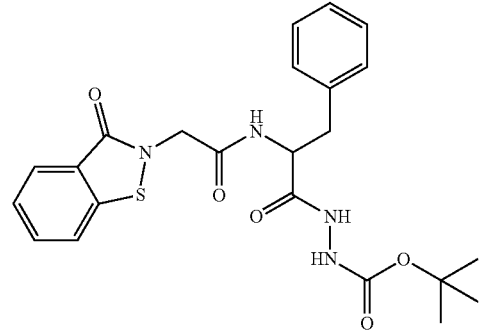

A second class of compounds as described herein includes isoindolinone compounds represented by Compound II:

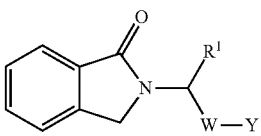

or pharmaceutically acceptable salts or prodrugs thereof.

In Compound II, $R^1$ is hydrogen or methyl.

Also in Compound II, W is —C(O)$NR^2$—, —C(O)$NR^3$—$NR^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In some examples, W is —C(O)NH—, —C(O)$NCH_3$—, or —C(O)NH—NHC(O)—. In some examples, W is

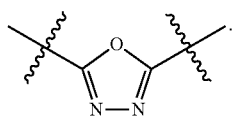 [SMILES: *c1nnc(*)o1]

Additionally in Compound II, Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, Y is substituted or unsubstituted benzyl, substituted or unsubstituted aryl, methyl, or amino. The Y group of Compound II can have, for example, one of the Structures A1-A4.

In one example of Compound II, when $R^1$ is methyl, W—Y is not

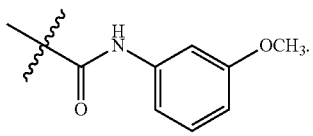 [SMILES: *C(=O)Nc1cccc(OC)c1]

A third class of compounds as described herein includes 1,2-benzisothiazolinone compounds represented by Compound III:

I-20
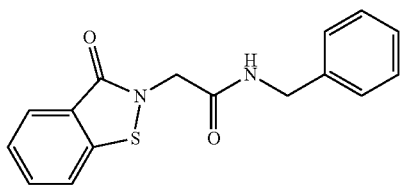

I-21
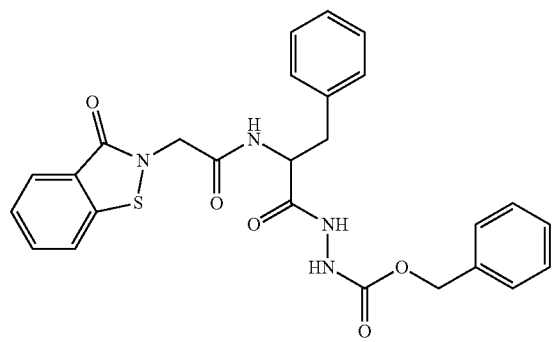

I-22
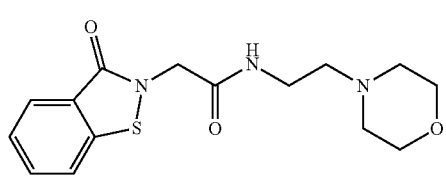

I-23
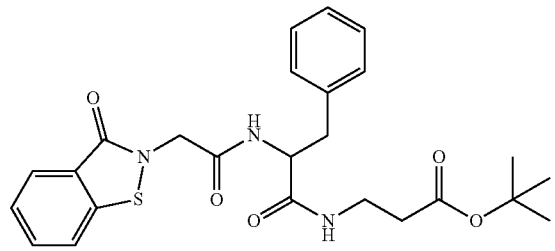

I-24
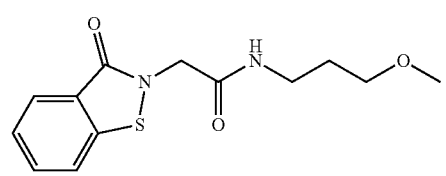

I-25
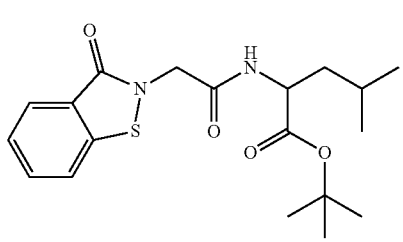

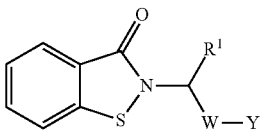

III or pharmaceutically acceptable salts or prodrugs thereof.

In Compound III, $R^1$ is hydrogen or methyl.

Also in Compound III, W is —C(O)NR$^2$—, —C(O)NR$^3$—NR$^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In some examples, W is —C(O)NH—, —C(O)NCH$_3$—, or —C(O)NH—NHC(O)—. In some examples, W is

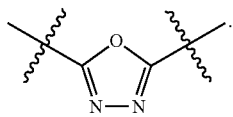 [SMILES: *c1nnc(*)o1]

Additionally in Compound III, Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, Y is substituted or unsubstituted benzyl, substituted or unsubstituted aryl, methyl, or amino. The Y group of Compound III can have, for example, one of the Structures A1-A4.

In one example of Compound III, when $R^1$ is methyl, W—Y is not

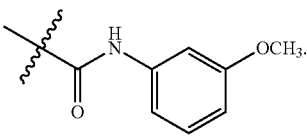 [SMILES: *C(=O)Nc1cccc(OC)c1]

In an additional example of Compound III, when $R^1$ is hydrogen, W—Y is not

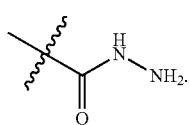

In a further example of Compound III, when $R^1$ is methyl, W—Y is not

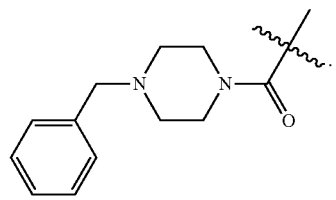 [SMILES: *C(=O)N1CCN(Cc2ccccc2)CC1]

A fourth class of compounds as described herein includes 1,2-benzisothiazolinone compounds represented by Compound IV:

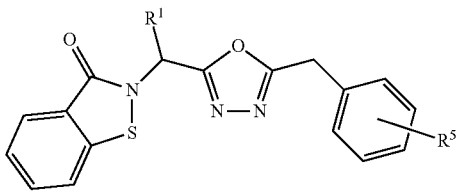

IV or pharmaceutically acceptable salts or prodrugs thereof.

In Compound IV, $R^1$ is hydrogen or methyl. In some examples, $R^1$ is hydrogen.

Also in Compound IV, $R^5$ is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, $R^5$ is hydrogen or methoxy. In some examples, the $R^5$ group is located in a para position.

A fifth class of compounds as described herein includes 1,2-benzisothiazolinone compounds represented by Compound V:

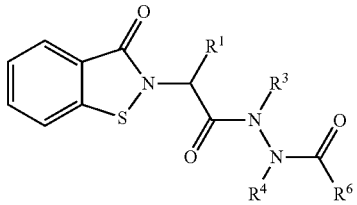

V or pharmaceutically acceptable salts or prodrugs thereof.

In Compound V, $R^1$ is hydrogen or methyl. In some examples, $R^1$ is hydrogen.

Also in Compound V, $R^3$ and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In some examples, $R^3$ is hydrogen. In some examples, $R^4$ is hydrogen.

Additionally in Compound V, $R^6$ is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, $R^6$ is methyl, benzyl, m-chlorophenyl, or p-methoxybenzyl.

A sixth class of compounds as described herein includes 1,2-benzisothiazolinone compounds represented by Compound VI:

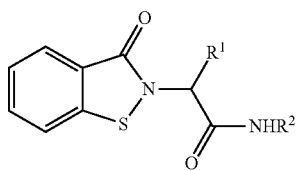

VI or pharmaceutically acceptable salts or prodrugs thereof.

In Compound VI, $R^1$ is hydrogen or methyl. In some examples, $R^1$ is hydrogen.

Also in Compound VI, $R^2$ is hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, $R^2$ is a substituted alkyl group. In some examples, $R^2$ is (o-methoxy)phenyl, benzyl, (alpha-methyl)phenyl, N—(2-ethylmorpholine), or (3-methoxy)propyl.

In one example of Compound VI, when $R^1$ is methyl, $R^3$ is not

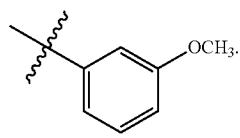 [SMILES: *c1cccc(OC)c1]

A seventh class of compounds as described herein includes 1,2-benzisothiazolinone compounds represented by Compound VII:

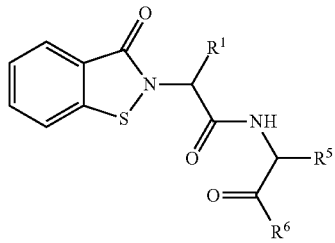

VII or pharmaceutically acceptable salts or prodrugs thereof.

In Compound VII, $R^1$ is hydrogen or methyl. In some examples, $R^1$ is hydrogen.

Also in Compound VII, $R^5$ and $R^6$ are each independently selected from hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, $R^5$ is hydrogen, benzyl, or isobutyl. In some examples, $R^6$ is hydroxy, —NHOH, —NHNHCO$_2$tBu, —NHNHCO$_2$Bn, or —NH(CH$_2$)$_2$CO$_2$tBu.

Also described herein is a 1,2-benzisothiazolinone compound of the following formula:

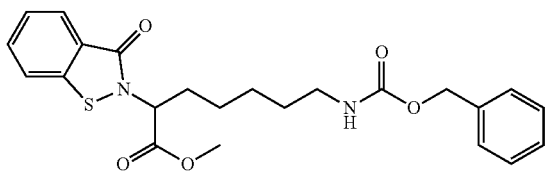 [SMILES: COC(=O)C(CCCCCNC(=O)OCc1ccccc1)n1sc2ccccc2c1=O]

or pharmaceutically acceptable salts and prodrugs thereof.

As used herein, the terms alkyl, alkenyl, and alkynyl include straight- and branched-chain monovalent substituents. Examples include methyl, ethyl, isobutyl, 3-butynyl, and the like. Heteroalkyl, heteroalkenyl, and heteroalkynyl are similarly defined but may contain O, S, or N heteroatoms or combinations thereof within the backbone. The term cycloalkyl as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term heterocycloalkyl is a type of cycloalkyl group as defined above, and is included within the meaning of the term cycloalkyl, where at least one of the carbon atoms of the ring is replaced with a heteroatom such as, but not limited to, nitrogen, oxygen, sulfur, or phosphorus.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system.

Examples of heteroaryl molecules include, furan, pyrrole, thiophene, imidazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, cycloalkyl, aryl, heteroalkyl, heteroalkenyl, heteroalkynyl, heterocycloalkyl, and heteroaryl molecules used herein can be substituted or unsubstituted. As used herein, the term substituted includes the addition of an alkyl, alkenyl, alkynyl, cycloalkyl, aryl, heteroalkyl, heteroalkenyl, heteroalkynyl, heterocycloalkyl, or heteroaryl group (as described herein) to a position attached to the main chain of the alkyl, alkenyl, alkynyl, cycloalkyl, aryl, heteroalkyl, heteroalkenyl, heteroalkynyl, heterocycloalkyl, or heteroaryl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, cycloalkyl, aryl, heteroalkyl, heteroalkenyl, heteroalkynyl, heterocycloalkyl, or heteroaryl has a full complement of hydrogens, i.e., commensurate with its saturation level, with no substitutions, e.g., linear decane ($-(CH_2)_9-CH_3$).

The compounds described herein may contain chiral centers. Such chiral centers may be of either the (R) or (S) configuration, or may be a mixture thereof. Thus, the compounds provided herein may be enantiomerically pure, or be stereoisomeric or diastereomeric mixtures. The separation of mixtures of optical isomers to obtain pure enantiomers is well known in the art and is contemplated. Enantiomeric resolution may, for example, be achieved by fractional crystallization of salts with chiral acids or by chromatographic separation on chiral columns.

In the case of amino acid residues, such residues may be of either the L- or D-form. As used herein, the term amino acid refers to α-amino acids which are racemic, or of either the D- or L-configuration. The designation "L" preceding an amino acid refers to the L-isomer of the amino acid. The designation "DL" preceding an amino acid designation refers to a mixture of the L- and D-isomers of the amino acid. The chiral centers of the compounds provided herein may undergo epimerization in vivo. As such, the administration of a compound in its (L) form is equivalent, for compounds that undergo epimerization in vivo, to administration of the compound in its (D) form.

The compounds described herein can be prepared in a variety of ways. The compounds can be synthesized using synthetic methods known in the art of synthetic organic chemistry or variations thereon as appreciated by those skilled in the art. The compounds described herein can be prepared from readily available starting materials. Optimum reaction conditions may vary with the particular reactants or solvent used, but such conditions can be determined by one skilled in the art by routine optimization procedures.

Variations on Compound I, Compound II, Compound III, Compound IV, Compound V, Compound VI, and Compound VII include the addition, subtraction, or movement of the various constituents as described for each compound. Similarly, as described above, when one or more chiral centers is present in a molecule the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4$^{th}$ Ed., Wiley & Sons, 2006, which is incorporated herein by reference in its entirety. The synthesis and subsequent testing of various compounds as described by Compound I, Compound II, Compound III, Compound IV, Compound V, Compound VI, and Compound VII to determine efficacy is contemplated.

Reactions to produce the compounds described herein can be carried out in solvents which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Examples of compounds described by Compound I, wherein X is S, Z is C=O, W is $-C(O)NR^2$, and Y is H; Compound III, wherein W is $-C(O)NR^2$, and Y is H; Compound VI; or Compound VII; and pharmaceutically acceptable salts and prodrugs thereof can be made using the methods shown in Scheme 1. In the synthesis of Compound VII, $R^2$ as shown in Scheme 1 is $-CH(R^5)C(O)R^6$.

Scheme 1:

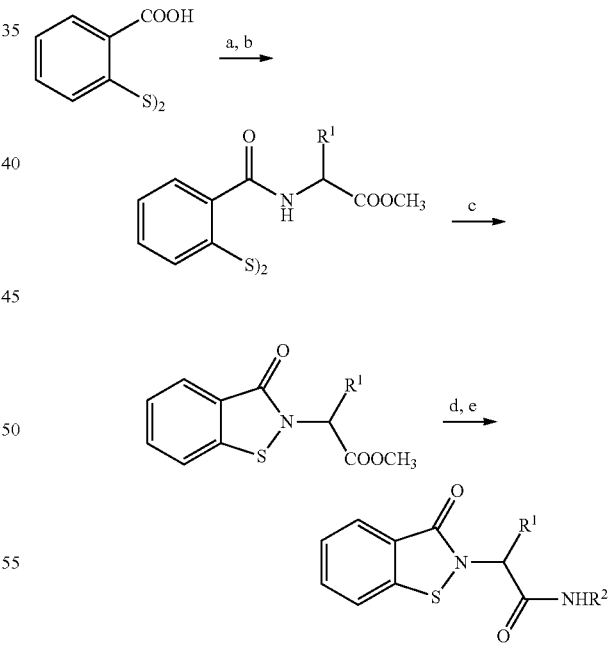

a. $SOCl_2$, reflux; b. (DL)$NH_2CHR^1COOCH_3$/$Et_3N$
c. $Br_2$/$Et_3N$; d. LiOH, aq. THF; e. EDCI/HOBt, then $R^2NH_2$ Examples of compounds described by Compound I, wherein X is $CH_2$, Z is C=O, W is $-C(O)NR^2$, and Y is H; or Compound II, wherein W is $-C(O)NR^2$, and Y is H; and pharmaceutically acceptable salts and prodrugs thereof can be made using the methods shown in Scheme 2.

Scheme 2:

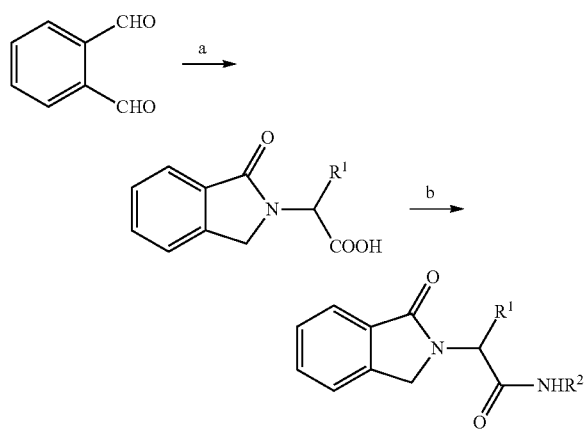

a. (DL)R$^1$CH(COOH)NH$_2$/CH$_3$CN/heat
b. EDCI/HOBt, then R$^2$NH$_2$

Examples of compounds described by Compound I, wherein Z is CO=W is —C(O)NR$^2$, wherein R$^2$ is a substituted triazole, and Y is H and pharmaceutically acceptable salts and prodrugs thereof can be made using the methods shown in Scheme 3. In Scheme 3, T represents a substitution group as described herein.

Scheme 3:

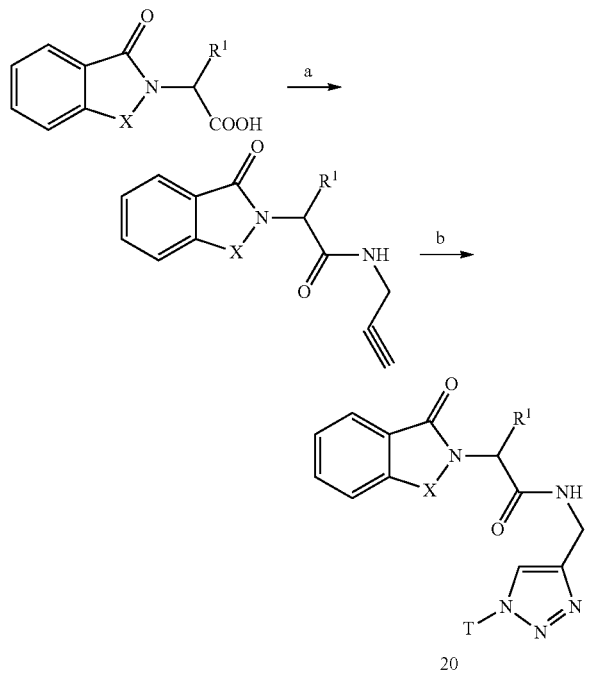

a. EDCI/HOBt, then propargyl amine;
b. T—N$_3$ /CuSO$_4$/ascorbate/t-BuOH

Examples of compounds described by Compound I, wherein Z is C=O and W is —C(O)NR$^3$—NR$^4$C(O)—, wherein R$^3$ and R$^4$ are H; Compound V; and pharmaceutically acceptable salts and prodrugs thereof can be made using the method shown in Scheme 4.

Scheme 4:

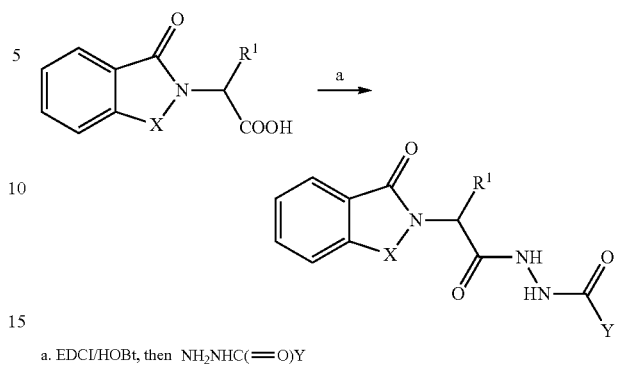

a. EDCI/HOBt, then NH$_2$NHC(=O)Y

Examples of compounds described by Compound I, wherein Z is C=O and W is a substituted or unsubstituted oxadiazole; Compound IV; and pharmaceutically acceptable salts and prodrugs thereof can be made using the method shown in Scheme 5.

Scheme 5:

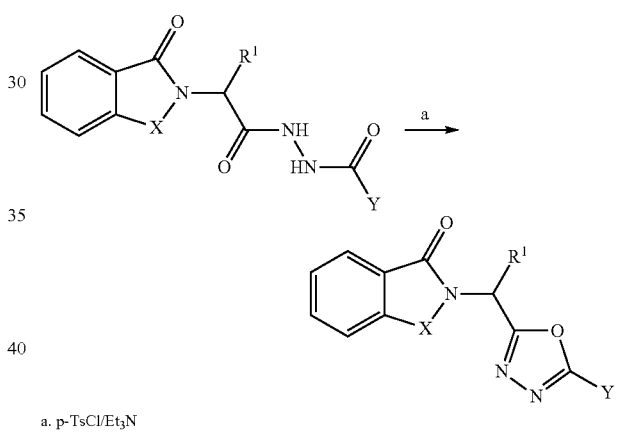

a. p-TsCl/Et$_3$N

The compounds described herein or pharmaceutically acceptable salts or prodrugs thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the compounds described herein or a pharmaceutically acceptable salt or prodrug thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected substrate without causing significant undesirable biological effects or interacting in a deleterious manner with any of the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compounds described herein or pharmaceutically acceptable salts or prodrugs thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration of the compounds described herein or a pharmaceutically acceptable salt or prodrug thereof include capsules, tablets, pills, powders, and granules. In such solid dosage forms, the compounds described herein or a pharmaceutically acceptable salt or prodrug thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting, emulsifying, suspending, sweetening, flavoring, or perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are preferably suppositories which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, and inhalants. The compounds described herein or pharmaceutically acceptable salts or prodrugs thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of the compounds described herein that are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught therein.)

The compounds and compositions described above are useful in treating viral, fungal, or yeast infections in humans, e.g., including pediatric and geriatric populations, and animals, e.g., veterinary applications. Methods of using the compounds and compositions described herein comprise administering to a subject a therapeutically effective amount of the compounds or compositions described herein or a pharmaceutically acceptable salt or prodrug thereof. Viral infections include, for example, Hepatitis C Virus and Flavivirus infections. Flavivirus infections include, for example, West Nile Virus, Dengue Virus, and Japanese Encephalitis Virus. Several serotypes of Dengue Virus have been identified such as, for example, serotype DEN-1, serotype DEN-2, serotype DEN-3, and serotype DEN-4. Examples of yeast and fungal infections treatable by the methods described herein include fluconazole-resistant infections and infections caused by the genus *Candida* (e.g., candidiasis, including vaginal candidiasis and hospital acquired candidiasis), and fluconazole-resistant infections and infections caused by the genus *Aspergillus fumigatus*. The methods described herein are useful in treating infections caused by several species of *Candida*, including *Candida albicans, Candida glabrata, Candidia parapsilosis, Candidia apicola*, and *Candida tropicalis*. Further, the methods of treating fungal or yeast infections as described herein are useful in treating immunocompromised subjects. Immunocompromised subjects include, for example, HIV-positive subjects; subjects undergoing immunotherapy; cancer patients; individuals with viral infections; individuals with an autoimmune disease; patients with malignancies, leukemias, collagen-vascular diseases, or congenital or acquired immunodeficiency; organ-transplant recipients receiving immunosuppressive therapy; and other patients receiving immunosuppressive therapy. As used herein the term treating or treatment includes prevention; delay in onset; diminution, eradication, or delay in exacerbation of signs or symptoms after onset; and prevention of relapse.

The methods and compounds or compositions as described herein are useful for both prophylactic and therapeutic treatment of viral, fungal, or yeast infections. For prophylactic use, a therapeutically effective amount of the compounds or compositions described herein are administered to a subject prior to exposure (e.g., before or when traveling to a location where viral, yeast, or fungal infections are possible), during a period of potential exposure to viral, yeast, or fungal infections, or after a period of potential exposure to viral, yeast, or fungal infections. Prophylactic administration can occur for several days to weeks prior to potential exposure, during a period of potential exposure, and for a period of time, e.g., several days to weeks, after potential exposure. Therapeutic treatment involves administering to a subject a therapeutically effective amount of the compounds or compositions described herein after a viral, yeast, or fungal infection is diagnosed.

Administration of compounds or compositions described herein or pharmaceutically acceptable salts or prodrugs thereof can be carried out using therapeutically effective amounts of the compounds or compositions described herein or pharmaceutically acceptable salts or prodrugs thereof for periods of time effective to treat viral, yeast, or fungal infections. The effective amount of the compounds or compositions described herein or pharmaceutically acceptable salts or prodrugs thereof may be determined by one of ordinary skill in the art, and includes exemplary dosage amounts for a mammal of from about 0.05 to about 100 mg/kg of body weight of active compound per day, which may be administered in a single dose or in the form of individual divided doses, such as from 1 to 4 times per day. Alternatively, the dosage amount can be from about 0.05 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In these methods, a viral, yeast, or fungal infection, for example, can be further treated with one or more additional agents. For example, the methods of treating and preventing viral, yeast, or fungal infections as described herein can further include administering a second compound or composition to the subject. In the treatment of viral infections, the second compound or composition can include an antiviral compound or mixtures of antiviral compounds (e.g., pegylated interferon-α, ribavirin, and mixtures thereof). The second compound or composition used in the treatment of fungal or yeast infections can include antifungal compounds, antiviral compounds, or mixtures thereof. Examples of second compounds include triazole antifungals, thiazole antifungals, imidazole antifungals, polyene antifungals, enchinocandin antifungals, allylamine antifungals, and amphotericin B. Antiviral compounds that can be used in combination with the compounds described herein include, for example, nucleoside polymerase inhibitors, non-nucleoside polymerase inhibitors, protease inhibitors, nucleoside or nucleotide reverse transcriptase inhibitors, non-nucleoside reverse transcriptase inhibitors, entry inhibitors, assembly inhibitors, integrase inhibitors, kinase inhibitors, enzyme inhibitors, maturation inhibitors, M2 inhibitors, and neuraminidase inhibitors. Examples of such additional antiviral compounds include, but are not limited to amantadine, rimantadine, oseltamivir (Tamilfu®, Roche Laboratories, Nutley, N.J.), zanamivir (Relenza®, GlaxoSmithKline, Philadelphia, Pa.), peramivir, raltegravir, Maraviros, enfuviritide, bevirimat, Vivecon™ (Myriad Genetics, Salt Lake City, Utah), Combivir® (zidovudine+lamivudine, AZT+3TC) (GlaxoSmithKline, Philadelphia, Pa.), Emtriva® (emtricitabine, FTC) (Gilead Sciences, Foster City, Calif.), Epivir® (lamivudine, 3TC) (GlaxoSmithKline, Philadelphia, Pa.), Epzicom® (Kivexa, abacavir+lamivudine, ABC+3TC) (GlaxoSmithKline, Philadelphia, Pa.), Retrovir® (zidovudine, AZT, ZDV) (GlaxoSmithKline, Philadelphia, Pa.), Trizivir® (abacavir+zidovudine+lamivudine, ABC+AZT+3TC) (GlaxoSmithKline, Philadelphia, Pa.), Truvada® (tenofovir DF+emtricitabine, TDF+FTC) (Gilead Sciences, Foster City, Calif.), Videx® & Videx EC® (didanosine, ddI) (Bristol-Myers Squibb, Princeton, N.J.), Viread® (tenofovir disoproxil fumarate, TDF) (Gilead Sciences, Foster City, Calif.), Zerit® (stavudine, d4T) (Bristol-Myers Squibb, Princeton, N.J.), Ziagen® (abacavir, ABC) (GlaxoSmithKline, Philadelphia, Pa.), Racivir™ (RCV) (Pharmasset, Princeton, N.J.), Amdoxovir™ (AMDX, DAPD) (RFS Pharma, Tucker, Ga.), apricitabine (SPD754, AVX754), elvucitabine (ACH-126, 443, Beta-L-Fd4C), Immunitin® (HE2000, alpha-epibromide) (Hollis-Eden Pharmaceuticals, San Diego, Calif.), Proleukin® (aldesleukin, Interleukin-2, IL-2) (Chiron Corporation, Emeryville, Calif.), Remune® (HIV-1 Immunogen, Salk vaccine) (Orchestra Therapeutics, Carlsbad, Calif.), BAY 50-4798, IR103, Intelence™ (etravirine, TMC-125) (Tibotec Therapeutics, Irvine, Calif.), Rescriptor® (delavirdine, DLV) (Pfizer, New York, N.Y.), Sustiva® (Stocrin, efavirenz, EFV) (Bristol-Myers Squibb, Princeton, N.J.), Viramune® (nevirapine, NVP) (Boehringer Ingelheim, Ridgefield, Conn.), rilpivirine (TMC-278), Agenerase® (amprenavir, APV) (GlaxoSmithKline, Philadelphia, Pa.), Aptivus® (tipranavir, TPV) (Boehringer Ingelheim, Ridgefield, Conn.), Crixivan® (indinavir, IDV) (Merck, Whitehouse Station, N.J.), Invirase® (saquinavir, SQV) (Roche Laboratories, Nutley, N.J.), Kaletra® (Aluvia®, lopinavir/ritonavir, LPV/r) (Abbott Laboratories, Abbott Park, Ill.), Lexiva® (Telzir®, fosamprenavir, FPV) (GlaxoSmithKline, Philadelphia, Pa.), Norvir® (ritonavir, RTV) (Abbott Laboratories, Abbott Park, Ill.), Prezista® (darunavir, DRV) (Tibotec Therapeutics, Irvine, Calif.), Reyataz® (atazanavir, ATV) (Bristol-Myers Squibb, Princeton, N.J.), Viracept® (nelfinavir, NFV) (Pfizer, Inc., New York, N.Y.), Fuzeon® (enfuvirtide, ENF, T-20) (Roche Laboratories, Inc., Nutley, N.J.), Selzentry® (Celsentri®, maraviroc, UK-427,857) (Pfizer, Inc., New York, N.Y.), Vicriviroc® (SCH-417690, SCH-D) (Schering-Plough, Kenilworth, N.J.), PRO140 (Progenics Pharmaceuticals, Tarrytown, N.Y.), TNX-355 (Tanox, Inc., Houston, Tex.), Isentress® (raltegravir, MK -0518) (Merck, Whitehouse Station, N.J.), Elvitegravir™ (GS-9137) (Gilead Sciences, Foster City, Calif.), Bevirimat™ (PA-457) (Panacos Pharmaceuticals, Inc., Watertown, Mass.), and Droxia® or Hydrea® (hydroxyurea, HU) (Bristol-Myers Squibb, Princeton, N.J.).

The one or more additional agents and the compounds or compositions described herein or a pharmaceutically acceptable salt or prodrug thereof can be administered in any order, including simultaneous administration, as well as temporally spaced order of up to several days apart. The methods may also include more than a single administration of the one or more additional agents and/or the compounds or compositions described herein or a pharmaceutically acceptable salt or prodrug thereof. The administration of the one or more additional agent and the compounds or compositions described herein or a pharmaceutically acceptable salt or prodrug thereof may be by the same or different routes and concurrently or sequentially.

The examples below are intended to further illustrate certain aspects of the methods, compounds, and compositions described herein, and are not intended to limit the scope of the claims.

EXAMPLES

Example 1

Anti-fungal/Anti-yeast Activity

The anti-fungal or anti-yeast activity of Compounds I-1, I-2, I-3, I-4, I-5, I-6, and I-7 against *Candida* species, including *Candida albicans*, *Candida tropicalis*, *Candida glabrata*, *Candida lusitaniae*, *Candida parapsilosis*, and *Candida apicola*, as well as *Aspergillus fumigatus* was determined based upon the minimum inhibitory concentration (MIC) and minimum fungicidal concentrations (MFC) values as described below. An MFC/MIC ratio of less than four indicates that the compound is fungicidal; an MFC/MIC ratio of greater than four indicates that the compound is fungistatic. Fluconazole, an ergosterol inhibitor, and the beta-1,3-glucan inhibitor micafungin served as controls (See Tables 1-8).

MIC Determination—Broth Microdilution Method

The minimum inhibitory concentrations resulting in 50% growth inhibition ($MIC_{50}$) of three *Candida* species (*C. albicans*, *C. tropicalis* and *C. glabrata*, *C. lusitaniae*, *C. parapsilosis*, and *C. apicola*) as well as *Aspergillus fumigatus* to a set of novel synthetic compounds was determined in accordance with the guidelines in CLSI document M27-A2 (Clinical and Laboratory Standards Institute; Wayne, Pa.). The total volume of cells and drug was 100 µL per microtiter well, and each drug was diluted in RPMI to achieve final concentrations of 0.2-100 µg/ml. Uninoculated cultures were used as a reference standard. Stock inoculum suspensions were prepared from 24 hour cultures on YPD (yeast extract/peptone/dextrose) media at 30° C. For MIC determinations, an inoculum of $1.0 \times 10^3$ cells of *Candidia* and $2.0 \times 10^3$ cells of *Aspergillus* per well were used, and cells in diluted drugs were prepared in RPMI-1640 medium. MICs were determined both visually and spectrophotometrically at 24 hours and 48 h at 550 nm using a micro plate reader. The $MIC_{50}$ endpoint was measured as the lowest drug concentration resulting in a reduction of growth of 50% or more compared with growth of the control.

MFC Determination

Plating Method

The minimum fungicidal concentrations (MFCs) were determined for each drug-isolate-medium combination as follows. After 48 hours of incubation, 100 µL of each drug-isolate-medium combination (2 plates) was subcultured onto YPD plates (100 µL of solution was spread over the YPD plate). The subcultured solutions were obtained from each well that showed complete inhibition (100% or an optically clear well) from the last positive well (growth similar to that for the growth control well) and from the growth control (drug-free medium). The plates were then incubated at 30° C. for 48 hours. FIG. 1 displays YPD plates containing varying amounts of Compound I-5 and *C. glabrata*. The MFC was measured as the lowest drug concentration that showed either no growth or fewer than five colonies to obtain approximately 99% killing activity.

By Drop Plate Method/Spot Method

Figure 2:
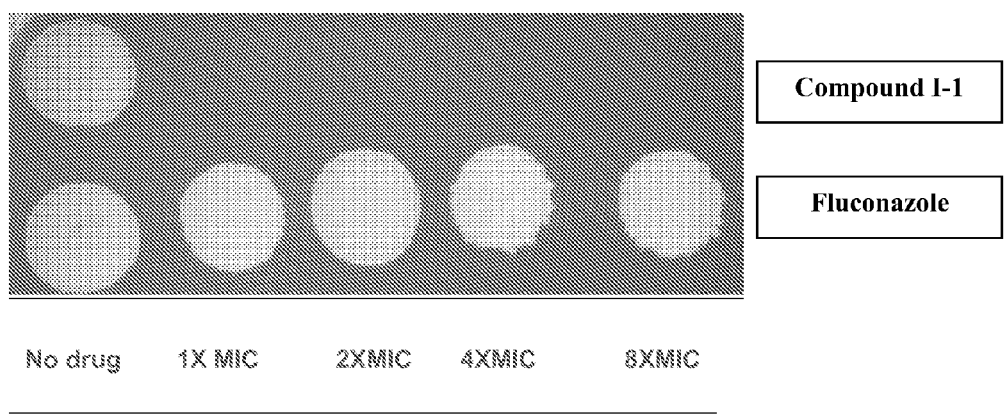
FIG. 2 is a picture of YPD plates used to determine activity by the drop plate method/spot method.

The in vitro fungicidal activities (MFCs) were determined for each drug-isolate-medium combination as follows. After 48 hours of incubation, 10 μL each drug-isolate-medium combination was spotted onto YPD plates (10 μL of each well is spotted sequentially with positive and negative control wells). The spotted solutions were obtained from each well that showed complete inhibition (100% or an optically clear well), from the last positive well (growth similar to that for the growth control well), and from the growth control (drug-free medium). The plates were then incubated at 30° C. for 48 hours. FIG. 2 displays a spot test using Compound I-1 and the CAF-2 strain of *C. albicans*. The MFC was measured as the lowest drug concentration that showed no growth.

TABLE 1

Activity against *Candida albicans* (CAF-2)

| Compounds | MIC-50 (μg/mL) | MFC (μg/mL) | Ratio MFC/MIC | Activity (fungicidal/fungistatic) |
|---|---|---|---|---|
| I-1 | 3.2 | 6.0 | 2 | fungicidal |
| I-2 | 3.2 | 3.2 | 1 | fungicidal |
| I-3 | 12.5 | 12.5 | 1 | fungicidal |
| I-4 | 6.4 | 6.4 | 1 | fungicidal |
| I-5 | 6.4 | 12.5 | 2 | fungicidal |
| I-6 | 12.5 | 12.5 | 1 | fungicidal |
| I-7 | 6.4 | 6.4 | 1 | fungicidal |
| Fluconazole | 0.25 | 5.0 | 20 | fungistatic |
| Micafungin | 0.016 | 0.016 | 1 | fungicidal |

TABLE 2

Activity against *Candida glabrata*

| Compounds | MIC-50 (μg/mL) | MFC (μg/mL) | Ratio MFC/MIC | Activity (fungicidal/fungistatic) |
|---|---|---|---|---|
| I-1 | 6.2 | 12.5 | 2 | fungicidal |
| I-2 | 1.6 | 3.2 | 2 | fungicidal |
| I-3 | 25.0 | 50.0 | 2 | fungicidal |
| I-4 | 12.5 | 12.5 | 1 | fungicidal |
| I-5 | 6.4 | 6.4 | 1 | fungicidal |
| I-6 | 12.5 | 12.5 | 1 | fungicidal |
| I-7 | 25.0 | 50.0 | 2 | fungicidal |
| Fluconazole | 6.2 | 50.0 | 9 | fungistatic |
| Micafungin | 0.016 | 0.016 | 1 | fungicidal |

TABLE 3

Activity against *Candida tropicalis*

| Compounds | MIC-50 (μg/mL) | MFC (μg/mL) | Ratio MFC/MIC | Activity (fungicidal/fungistatic) |
|---|---|---|---|---|
| I-1 | 3.2 | 3.2 | 1 | fungicidal |
| I-2 | 3.2 | 3.2 | 1 | fungicidal |
| I-3 | 6.4 | 12.5 | 2 | fungicidal |
| I-4 | 12.5 | 12.5 | 1 | fungicidal |
| I-5 | 6.4 | 12.5 | 2 | fungicidal |
| I-6 | 12.5 | 12.5 | 1 | fungicidal |
| I-7 | 12.5 | 12.5 | 1 | fungicidal |
| Fluconazole | 20.0 | 100.0 | 5 | fungistatic |
| Micafungin | 0.016 | 0.032 | 2 | fungicidal |

TABLE 4

Activity against *Saccharomyces cerevisiae* (YPH501)

| Compounds | MIC-50 (μg/mL) | MFC (μg/mL) | Ratio MFC/MIC | Activity (fungicidal/fungistatic) |
|---|---|---|---|---|
| I-1 | 1.6 | 3.2 | 2 | fungicidal |
| I-2 | 1.6 | 3.2 | 2 | fungicidal |
| I-3 | 12.5 | 12.5 | 1 | fungicidal |
| I-4 | 6.0 | 6.0 | 1 | fungicidal |
| I-5 | 3.0 | 3.0 | 1 | fungicidal |
| I-6 | 12.5 | 12.5 | 1 | fungicidal |
| I-7 | 12.5 | 12.5 | 1 | fungicidal |
| Fluconazole | 10.0 | 10.0 | 1 | fungicidal |
| Micafungin | 0.032 | 0.064 | 2 | fungicidal |

TABLE 5

Activity against *Candidia parapsilosis*

| Compounds | MIC-50 (μg/mL) | MFC (μg/mL) | Ratio MFC/MIC | Activity (fungicidal/fungistatic) |
|---|---|---|---|---|
| I-1 | 3.2 | 3.2 | 1 | fungicidal |
| I-2 | 1.6 | 3.2 | 2 | fungicidal |
| I-3 | 6.4 | 12.5 | 2 | fungicidal |
| I-4 | 12.5 | 12.5 | 1 | fungicidal |
| I-5 | 6.4 | 12.5 | 2 | fungicidal |
| I-6 | 12.5 | 12.5 | 1 | fungicidal |
| I-7 | 12.5 | 12.5 | 1 | fungicidal |
| Fluconazole | .4 | 4 | 10 | fungistatic |
| Micafungin | 0.4 | 3.2 | 8 | fungistatic |

TABLE 6

Activity against *Candida lusitaniae*

| Compounds | MIC-50 (μg/mL) | MFC (μg/mL) | Ratio MFC/MIC | Activity (fungicidal/fungistatic) |
|---|---|---|---|---|
| I-1 | 3.2 | 3.2 | 1 | fungicidal |
| I-2 | 1.6 | 3.2 | 2 | fungicidal |
| I-3 | 6.4 | 12.5 | 2 | fungicidal |
| I-4 | 12.5 | 12.5 | 1 | fungicidal |
| I-5 | 3.2 | 6.4 | 2 | fungicidal |
| I-6 | 12.5 | 12.5 | 1 | fungicidal |
| I-7 | 12.5 | 12.5 | 1 | fungicidal |
| Fluconazole | 3.2 | 25.0 | 8 | fungistatic |
| Micafungin | 0.032 | 0.032 | 1 | fungicidal |

TABLE 7

Activity against *Candida apicola*

| Compounds | MIC-50 (μg/mL) | MFC (μg/mL) | Ratio MFC/MIC | Activity (fungicidal/fungistatic) |
|---|---|---|---|---|
| I-1 | 3.2 | 3.2 | 1 | fungicidal |
| I-2 | 6.4 | 6.4 | 1 | fungicidal |
| I-3 | 6.4 | 12.5 | 2 | fungicidal |
| I-4 | 12.5 | 12.5 | 1 | fungicidal |
| I-5 | 6.4 | 12.5 | 2 | fungicidal |
| I-6 | 12.5 | 12.5 | 1 | fungicidal |
| I-7 | 12.5 | 12.5 | 1 | fungicidal |
| Fluconazole | 0.2 | 1.0 | 5 | fungistatic |
| Micafungin | 0.016 | 0.032 | 2 | fungicidal |

TABLE 8

Activity against *Aspergillus fumigatus*

| Compounds | MIC-50 (µg/mL) | MFC (µg/mL) | Ratio MFC/MIC | Activity (fungicidal/fungistatic) |
|---|---|---|---|---|
| I-1 | 25.0 | 100.0 | 4 | fungistatic |
| I-2 | 12.5 | 50.0 | 4 | fungistatic |
| I-3 | 6.4 | 12.5 | 2 | fungicidal |
| Fluconazole | 30.0 | 200.0 | 7 | fungistatic |
| Micafungin | 1.0 | 8.0 | 8 | fungistatic |

The $MIC_{50}$ of Compounds I-1, I-2, and I-5 in several mutant strains of *Candida albicans*, including fluconazole resistant clinical strains, was determined according to the methods described in Example 1 (see Table 9). The activity of Compound I-1 against fluconazole resistant strains was further explored (see Table 10). In Table 10, Strain #1 is a fluconazole sensitive *Candida albicans* strain; Strain #17 is a fluconazole resistant *Candida albicans* strain; *C. albicans* CS#01 is a first clinical strain; *C. albicans* CS#02 is a second clinical strain.

TABLE 9

Activity of Compounds I-1, I-2, and I-5 in *C. albicans* Mutants

| Strains | Compound I-2 $MIC_{50}$ (µg/mL) | Compound I-1 $MIC_{50}$ (µg/mL) | Compound I-5 $MIC_{50}$ (µg/mL) |
|---|---|---|---|
| CAF-2 | 3.0 | 3.0 | 6.0 |
| CHK21 | >100 | 3.0 | 6.0 |
| CHK23 | 25.0 | 3.0 | 6.0 |
| CHK11 | 12.5 | 3.0 | 6.0 |
| GOA31 | 3.0 | 6.0 | 6.0 |
| GOA32 | 3.0 | 3.0 | 6.0 |

TABLE 10

Activity of Compound I-1 Against Fluconazole Resistant *C. albicans*

| | Strains, $MIC_{50}$ (µg/mL) | | | |
|---|---|---|---|---|
| Compounds | #1 | #17 | *C. albicans* CS#01 | *C. albicans* CS#02 |
| Fluconazole | 0.8 | >100 | 1.6 | 1.6 |
| I-1 | 3.0 | 6.0 | 3.0 | 3.0 |

Figure 4:
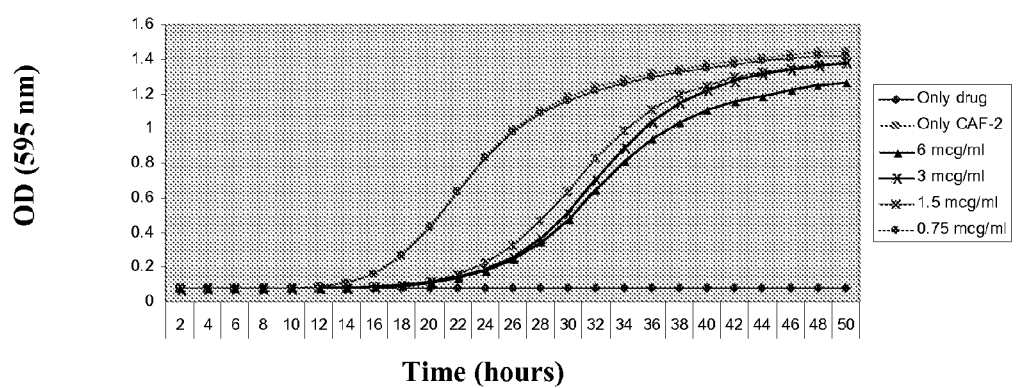
FIG. 4 is a graph displaying the dose response inhibition of *C. albicans* strain CAF-2 by Compound I-1.
Figure 5:
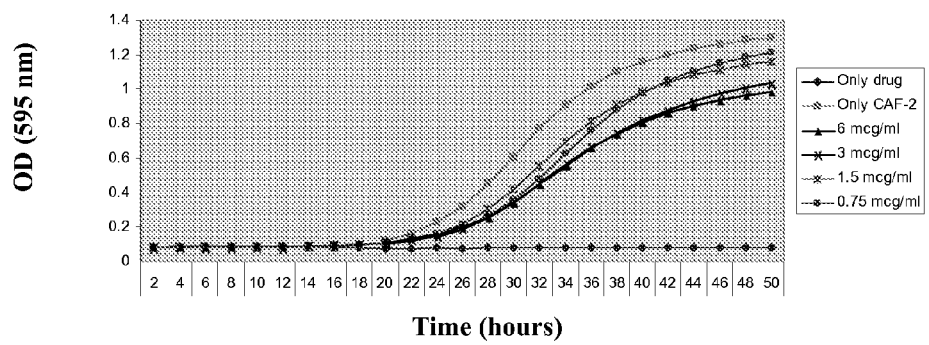
FIG. 5 is a graph displaying the dose response inhibition of *C. albicans* strain CAF-2 by Compound I-2.

The dose response inhibition of *C. albicans* strain CAF-2 by Compounds I-1 and I-2 was also determined (FIGS. 4 and 5).

Example 2

Toxicity Assays

Neutral Red Uptake Assay

Figure 3:
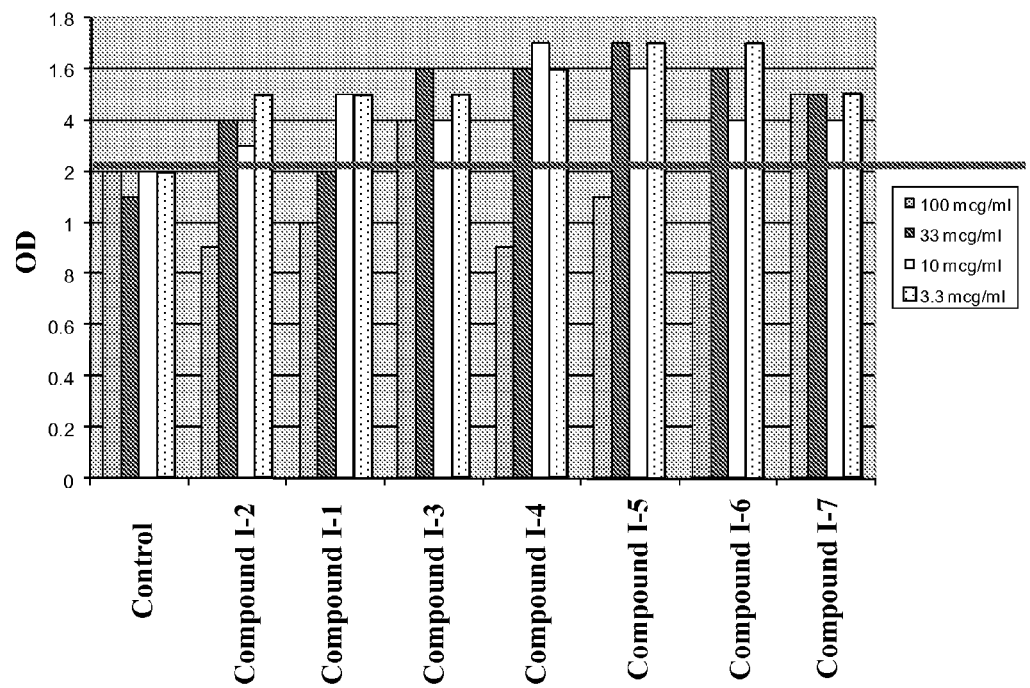
FIG. 3 is a bar graph showing the toxicity of Compounds I-1, I-2, I-3, I-4, I-5, I-6, and I-7 at various concentrations compared to a control according to the neutral red assay.

The neutral red uptake assay is a cytotoxicity test that is based on the ability of viable cells to incorporate and bind the supra-vital dye neutral red in the lysosomes. This weakly cationic dye penetrates cell membranes by non-ionic passive diffusion and concentrates in the lysosomes, where it binds by electrostatic hydrophobic bonds to anionic and phosphate groups of the lysosomal matrix. The dye is then extracted from the viable cells using an acidified ethanol solution, and the absorbance of the solubilized dye is read. When the cell dies or the pH gradient is reduced, the dye is not retained and consequently, the amount of retained dye is proportional to the number of viable cells. Most primary cells and cell lines can be used for this method. The HepG2 and Huh7, two human hepatoma cell lines, were used for this study. The cells were seeded in 96-well tissue culture plates and treated for 48 hours with the compounds. The plates were then incubated for 2 hours with a medium containing neutral red. The cells were subsequently washed, the dye was extracted in each well, and the absorbance was read using a spectrophotometer (FIG. 3 and Table 11). None of the compounds displayed toxicity after 24 hours at concentrations of 3.3 µg/mL, 10 µg/mL, 33 µg/mL, and 100 µg/mL.

TABLE 11

Neutral Red Assay; Percentage Viability of Huh7 cells

| | Percentage Viability | | | |
|---|---|---|---|---|
| Compounds | 100 µg/mL (approx 30X MIC) | 33 µg/mL (approx 10X MIC) | 10 µg/mL (approx 3X MIC) | 3.3 µg/mL (approx 1X MIC) |
| I-1 | 83 | >100 | >100 | >100 |
| I-2 | 75 | >100 | >100 | >100 |
| I-3 | >100 | >100 | >100 | >100 |
| I-4 | 75 | >100 | >100 | >100 |
| I-5 | 92 | >100 | >100 | >100 |
| I-6 | 67 | >100 | >100 | >100 |
| I-7 | >100 | >100 | >100 | >100 |

MTT Assay

The MTT assay is a colorimetric assay that measures the reduction of yellow 3-(4,5-dimethylhiazol-2-yl)-2,5-diphenyl tetrazolium bromide (MTT) by mitochondrial succinate dehydrogenase. The MTT enters the cells and passes into the mitochondria where it is reduced to an insoluble, dark purple, formazan product. The cells are then solubilized with an organic solvent (e.g., isopropanol) and the released, solubilized formazan reagent is measured spectrophotometrically. Since reduction of MTT can only occur in metabolically active cells, the level of activity is a measure of the viability of the cells.

Cells of the Huh7 or HepG2 cell line were seeded in a 96 well plate. The plate was incubated overnight at 37° C. in a humidified incubator, 5% $CO_2$. The test compounds were added to the plate. Different concentrations of drug were tested in triplicate along with a negative control. The final volume was adjusted to 100 µl per well. The plate was incubated overnight at 37° C. in a humidified incubator, 5% $CO_2$. After 24 hours and 48 hours, MTT reagent (5 mg/ml, 10 µl/100 µl per well of the 96 well plate) was added and incubated at 37° C. for 3 hours. After 3 hours, 100 µl of the DMSO solution was added to each well and the plate was rocked at room temperature for 1 hour. The plate was then read on a plate reader at 550 nM. The MTT Assay data reflected the same trend as shown from the Neutral Red Assay data (see FIG. 3 and Table 11), and showed that Compounds I-1, I-2, I-3, I-4, I-5, I-6, and I-7 are minimally toxic to mammalian cell lines.

Example 3

Anti-HCV Activity of Compounds

Figure 6:
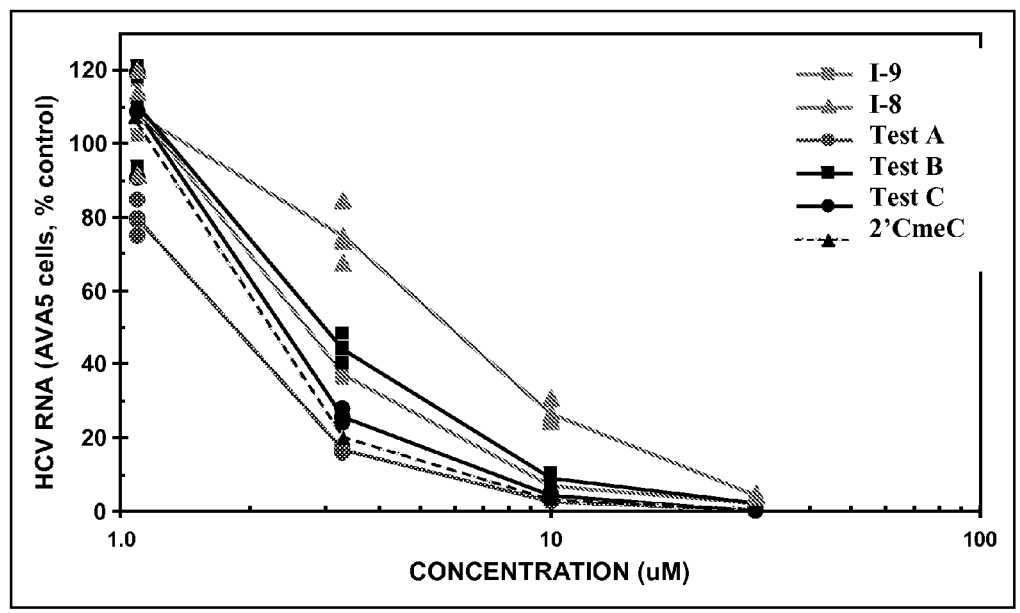
FIG. 6 is a graph displaying the dose response inhibition of HCV by Compounds I-8 and I-9.

The antiviral activity of Compounds I-8 and I-9 was assessed in a 3-day assay using the stably-expressing HCV replicon cell lines, AVA5 (sub-genomic CONI, genotype 1b) and APC103 (genomic H77, genotype 1a) maintained as sub-confluent cultures on 96-well plates. Antiviral activity was determined by blot hybridization analysis of intracellular HCV RNA (normalized to the level of cellular B-actin RNA in each culture sample). See Table 12. A 3-fold suppression of HCV RNA and less than 2-fold suppression of cellular B-actin RNA was used as the cutoff. Cytotoxicity was assessed by neutral red dye uptake after 3 days of treatment. Dose response inhibition of HCV was also determined (FIG. 6). The nucleoside analogue 2'C-methyl cytidine (2'CmeC) was used as an assay activity control. $EC_{50}$, $EC_{90}$ and $CC_{50}$ values (+/− standard deviations [S.D.]) were calculated by linear regression analysis. $EC_{50}$ and $EC_{90}$ are drug concentrations at which a 2-fold, or a 10-fold depression of intracellular HBV DNA or HCV RNA (relative to the average levels in untreated cultures), respectively, was observed. $CC_{50}$ is the drug concentration at which a 2-fold lower level of neutral red dye uptake (relative to the average levels in untreated cultures) was observed.

Analysis of combination therapies was performed using Calcusyn™ software (Biosoft, Inc.; Cambridge, UK). Two types of evaluations were performed (see FIG. 7). The top panels of FIG. 5 present CI-Fa (Combination Index—Fraction (of virus) affected) plots. For these plots, a combination index [CI] greater than 1.0 indicates antagonism and a CI less than 1.0 indicates synergism. Evaluations of synergy, additivity (summation), or antagonism at different levels of virus inhibition (e.g. 5% (Fa=0.5) to 99% (Fa=0.99)) were performed and are provided by the plotted lines and points. Dotted lines denoting 1.96 standard deviations for significance evaluations can be added but are not included in this example for clarity of presentation. The bottom panels present conservative isobolograms. For these plots, $ED_{50}$, $ED_{75}$, and $ED_{90}$ (50%, 75%, and 90% effective antiviral dose) values for the combination treatments are displayed as single points. Three lines radiating out from the axes denote the expected (e.g., additive) $EDC_{50}$, $EDC_{75}$, and $EDC_{90}$ values for drug combinations as calculated from the monotherapies. $ED_{50}$, $ED_{75}$, and $ED_{90}$ values for the combinations that plot to the left (e.g., less than) of the corresponding lines indicate synergy, and values plotting to the right (e.g., greater than) of the corresponding lines indicate antagonism.

Figure 7:
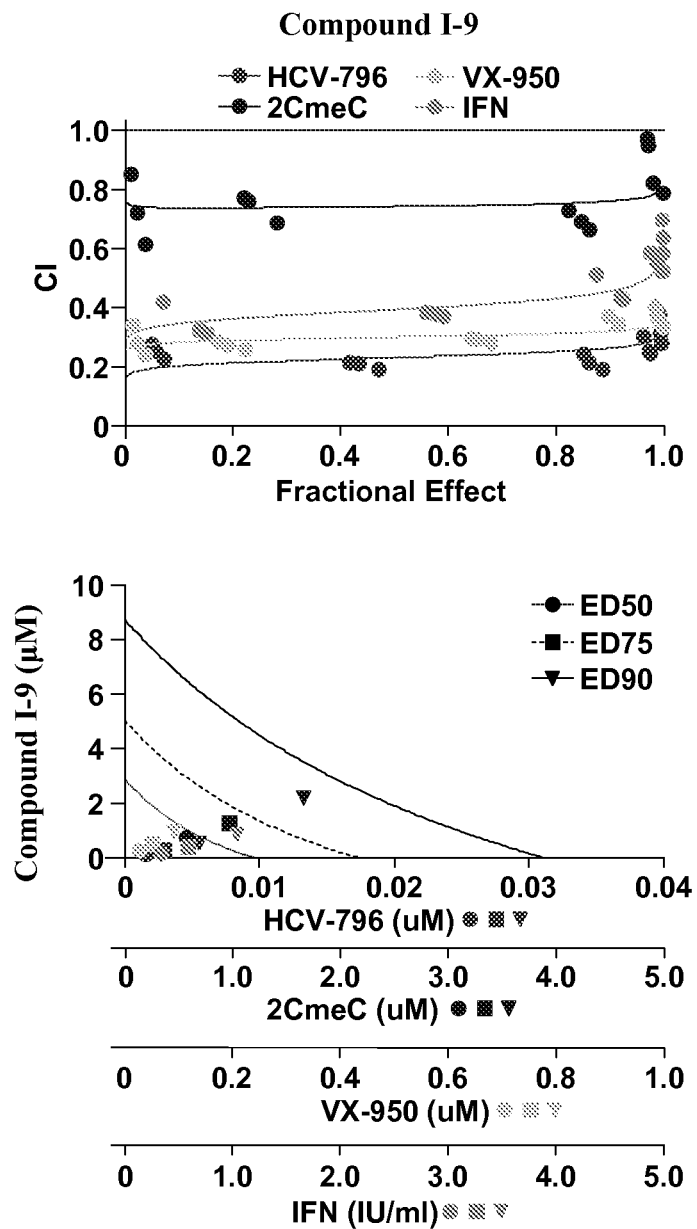
FIG. 7 is a graph displaying the analysis of Compound I-9 in combination treatments.

Compound I-9 interacted favorably with interferon, ribavirin, and the STAT-C agents as shown in Table 12 and FIG. 7. Various degrees of synergy were observed for the different combinations with each candidate compound (see FIG. 7 for an example). The addition of ribavirin (RBV) to the interferon combination did not lessen observed antiviral potencies, indicating that adverse interactions with this nucleoside are unlikely.

TABLE 12

HCV Inhibition by Compounds I-8 and I-9

| Compound | $CC_{50}$ (μM ± SD) | | $EC_{50}$ (μM ± SD) | | $EC_{90}$ (μM ± SD) | | SI ($CC_{50}/EC_{50}$) | |
|---|---|---|---|---|---|---|---|---|
| | AVA5 | APC103 | AVA5 | APC103 | AVA5 | APC103 | AVA5 | APC103 |
| I-8 | >100 | >100 | 5.8 ± 3.7 | 19 ± 2.3 | 5.6 ± 0.7 | 23 ± 1.8 | >17 | >18 |
| I-9 | >100 | >100 | 2.4 ± 0.2 | 8.5 ± 0.6 | 2.8 ± 0.3 | 9.0 ± 1.0 | >42 | >35 |
| 2'CmeC | >300 | >300 | 2.0 ± 0.1 | 5.8 ± 0.4 | 2.2 ± 0.2 | 6.4 ± 0.6 | >150 | >136 |

SI, Selectivity Index

Example 4

Anti-HCV Activity of Compound I-9 in Drug Combinations

Compound I-9 was utilized in combination treatments with interferon (with and without RBV), and several representative STAT—C agents including 2'CmeC (nucleoside analogue), HCV-796 (non-nucleoside polymerase inhibitor), and VX-950 (protease inhibitor) (Table 13). For these studies, the compounds were mixed at equipotent (not necessarily equimolar) concentrations based on the monotherapy $EC_{90}$ values. For example, 2'CmeC and Compound I-9 were mixed at equal molar concentrations, while 10-fold more Compound I-9 was used relative to VX-950 in that combination. The mixtures were then serially diluted for dose response analysis keeping the molar ratios constant. Corresponding monotherapies were also included. # Ribavirin (RBV) was held at a constant concentration of 30 uM for all serial dilutions of this combination. The overall type of interaction as determined by analysis with CalcuSyn (Biosoft, Inc.; Cambridge, UK) for each combination is indicated next to the corresponding EC50 and EC90 values in Table 13.

TABLE 13

Effect of Combination Treatments on HCV Replication

| Compound/Drug used for Combination | Molar Ratio | Compound I-9 (μM) | | Type of Interaction |
|---|---|---|---|---|
| | | $EC_{50}$ | $EC_{90}$ | |
| None (monotherapy) | N/A | 2.6 ± 0.2 | 9.1 ± 0.5 | N/A |
| IFN | 1:1 | 0.3 ± 0.03 | 1.0 ± 0.1 | S |
| IFN + 30 μM RBV[#] | 1:1 | 0.2 ± 0.03 | 0.7 ± 0.1 | S |
| 2'CmeC | 1:1 | 0.7 ± 0.1 | 1.8 ± 0.2 | S |
| HCV-796 | 1:100 | 0.1 ± 0.01 | 0.4 ± 0.03 | S |
| VX-950 | 1:10 | 0.3 ± 0.02 | 0.7 ± 0.1 | S |

S, synergistic

Example 5

Dose Response Inhibition of Compound I-5 in *C. glabrata*

*Candidia glabrata* cells from overnight cultures grown at 30° C. are diluted to a starting OD600 of 0.10 in 50 mL of YPD broth (e.g., Sigma-Aldrich, Co.; St. Louis, Mo.). As the MIC-50 of Compound I-5 with *C. glabrata* is 6.4 μg/mL, concentrations of 6.4 μg/mL (1×MIC), 12.5 μg/mL (2×MIC), 25.0 μg/mL (4×MIC), and 50.0 μg/mL (8×MIC) are added to four sets of 50 mL flasks containing the *C. glabrata* cells. One set of 50 mL flasks containing the *C. glabrata* cells is used as a control. The sets are run in quadruplicate. After Compound I-5 is added to the flasks, the cultures are incubated at 30° C. and the OD is recorded for 24 hours. Additionally, 1 mL of sample from each set is measured in a spectrophotometer at 600 nm every hour. The OD values are plotted against time in a semi-log plot. The dose response inhibition, time to effect, and effect on the log phase at different concentrations are determined from the characteristics of the semi-log plot.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus a combination of steps, elements, components, or constituents may be explicitly mentioned herein; however, all other combinations of steps, elements, components, and constituents are included, even though not explicitly stated.

What is claimed is:

1. A compound selected from the group consisting of:

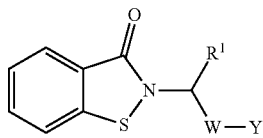

or a pharmaceutically acceptable salt or prodrug thereof, wherein:

$R^1$ is hydrogen or methyl;

W is —C(O)NR$^2$— or —C(O)NR$^3$—NR$^4$C(O)—, wherein R$^2$, R$^3$, and R$^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and Y is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalky wherein when W is C(O)NH, Y is selected from the group consisting of phenoxy substituted aryl and unsubstituted aryl;

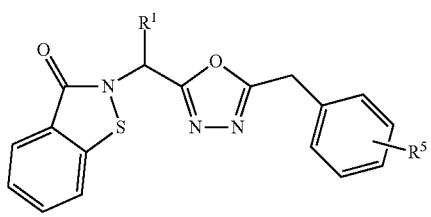

or a pharmaceutically acceptable salt or prodrug thereof, wherein:

$R^1$ is hydrogen or methyl; and $R^5$ is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl;

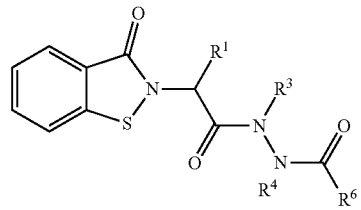

or a pharmaceutically acceptable salt or prodrug thereof, wherein:

$R^1$ is hydrogen or methyl;

$R^3$ and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and $R^6$ is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl;

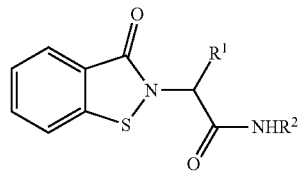

or a pharmaceutically acceptable salt or prodrug thereof, wherein:

$R^1$ is hydrogen or methyl; and $R^2$ is hydrogen, phenoxy-substituted aryl, or unsubstituted aryl;

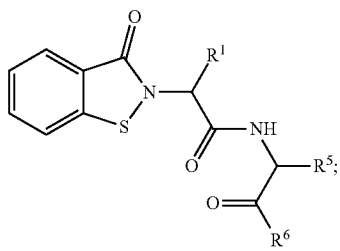

or a pharmaceutically acceptable salt or prodrug thereof, wherein:

$R^1$ is hydrogen or methyl; and $R^5$ and $R^6$ are each independently selected from hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkenyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and

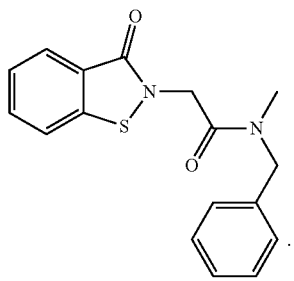 [SMILES: CN(Cc1ccccc1)C(=O)Cn1sc2ccccc2c1=O]

2. The compound of claim 1, wherein the compound has the following formula:

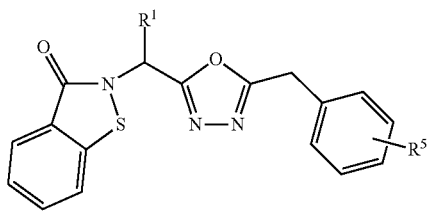

or a pharmaceutically acceptable salt or prodrug thereof, wherein:

$R^1$ is hydrogen or methyl; and $R^5$ is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

3. The compound of claim 1, wherein the compound has the following formula:

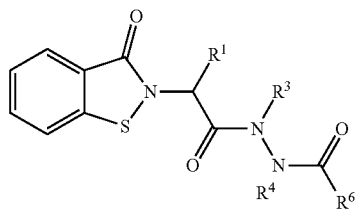

or a pharmaceutically acceptable salt or prodrug thereof, wherein:

$R^1$ is hydrogen or methyl;

$R^3$ and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and $R^6$ is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

4. The compound of claim 1, wherein the compound has the following formula:

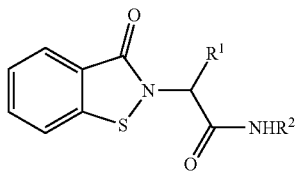

or a pharmaceutically acceptable salt or prodrug thereof, wherein:

$R^1$ is hydrogen or methyl; and $R^2$ is hydrogen, phenoxy-substituted aryl, or unsubstituted aryl.

5. The compound of claim 1, wherein the compound has the following formula:

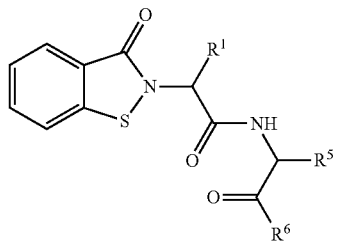

or a pharmaceutically acceptable salt or prodrug thereof, wherein:

$R^1$ is hydrogen or methyl; and $R^5$ and $R^6$ are each independently selected from hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

6. The compound of claim 1, wherein the compound has the following formula:

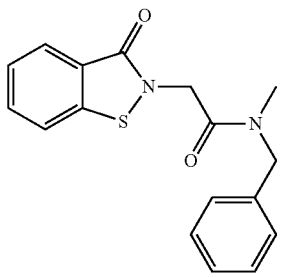 [SMILES: CN(Cc1ccccc1)C(=O)Cn1sc2ccccc2c1=O]

or a pharmaceutically acceptable salt or prodrug thereof.

7. The compound of claim 4, wherein the compound has the following formula:

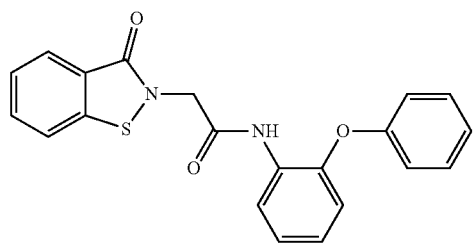 [SMILES: O=C(Cn1sc2ccccc2c1=O)Nc1ccccc1Oc1ccccc1]

or a pharmaceutically acceptable salt or prodrug thereof.

8. The compound of claim 2, wherein the compound has the following formula:

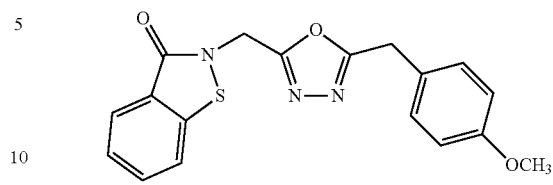

or a pharmaceutically acceptable salt or prodrug thereof.

9. The compound of claim 3, wherein the compound has the following formula:

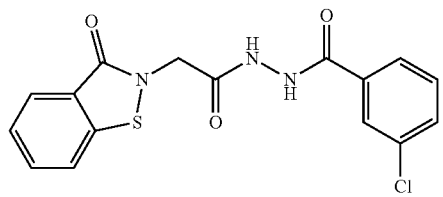 [SMILES: O=C(Cn1sc2ccccc2c1=O)NNC(=O)c1cccc(Cl)c1]

or a pharmaceutically acceptable salt or prodrug thereof.

10. The compound of claim 4, wherein the compound has the following formula:

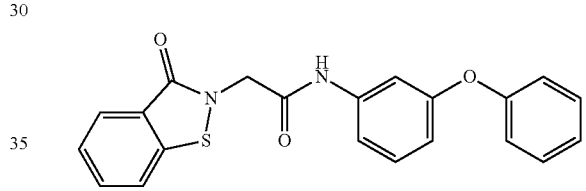

or a pharmaceutically acceptable salt or prodrug thereof.

11. The compound of claim 4, wherein the compound has the following formula:

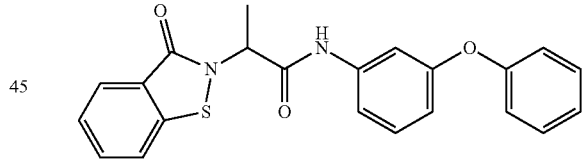

or a pharmaceutically acceptable salt or prodrug thereof.

12. A composition comprising a compound of claim 1 and a pharmaceutically acceptable carrier.

13. A method of diminishing an infection in a subject comprising administering to the subject a therapeutically effective amount of the compound selected from the group consisting of:

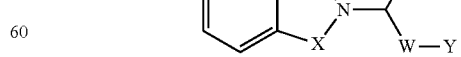

or a pharmaceutically acceptable salt or prodrug thereof, wherein:

$R^1$ is hydrogen or methyl;

W is —C(O)NR$^2$— or —C(O)NR$^3$—NR$^4$C(O)—, wherein R$^2$, R$^3$, and R$^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl;

X is S;

Y is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl; and Z is C=O;

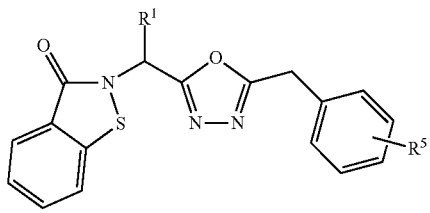

or a pharmaceutically acceptable salt or prodrug thereof, wherein:

$R^1$ is hydrogen or methyl; and $R^5$ is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl;

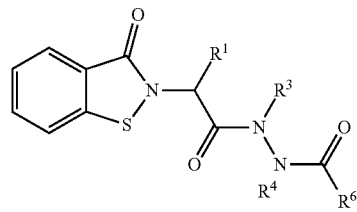

or a pharmaceutically acceptable salt or prodrug thereof, wherein:

$R^1$ is hydrogen or methyl;

$R^3$ and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and $R^6$ is hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl;

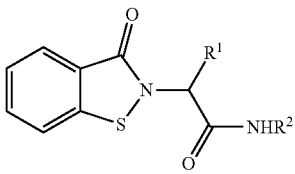

or a pharmaceutically acceptable salt or prodrug thereof, wherein:

$R^1$ is hydrogen or methyl; and $R^2$ is hydrogen, phenoxy-substituted aryl, or unsubstituted aryl;

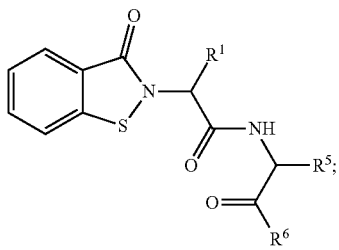

or a pharmaceutically acceptable salt or prodrug thereof, wherein:

$R^1$ is hydrogen or methyl; and $R^5$ and $R^6$ are each independently selected from hydrogen, hydroxy, alkoxy, substituted or unsubstituted amino, substituted or unsubstituted thiol, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkenyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and

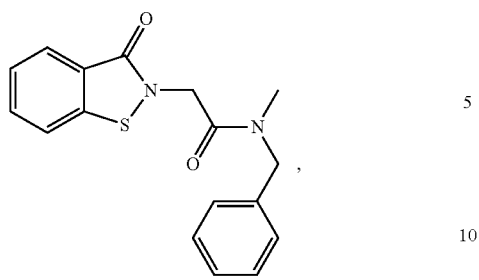

wherein the infection is Hepatitis C virus, a fungal infection, or a yeast infection wherein when W is C(O)NH, Y is selected from the group consisting of phenoxy substituted aryl and unsubstituted aryl.

14. The method of claim 13, wherein the infection is Hepatitis C Virus.

15. The method of claim 13, wherein the infection is a fungal infection.

16. The method of claim 15, wherein the fungal infection is candidiasis.

* * * * *

UNITED STATES PATENT AND TRADEMARK OFFICE
CERTIFICATE OF CORRECTION

PATENT NO. : 9,040,715 B2
APPLICATION NO. : 13/120602
DATED : May 26, 2015
INVENTOR(S) : Richard A. Calderone et al.

Page 1 of 1

It is certified that error appears in the above-identified patent and that said Letters Patent is hereby corrected as shown below:

In the claims,

Column 35, line 53, delete the text "heterocycloalkylalky" and insert the text --heterocycloalkylalkyl--

Column 37, line 8, delete the ";" appearing within the structure after "R5"

Column 37, line 21, delete the text "alkenyl" and insert the text --alkynyl--

Column 40, line 54, delete the text "the compound" and insert the text --a compound--

Column 42, line 46, delete the ";" appearing within the structure after "R5"

Column 42, line 60, delete the text "alkenyl" and insert the text --alkynyl--

Signed and Sealed this
Twenty-third Day of February, 2016

Michelle K. Lee
*Director of the United States Patent and Trademark Office*